(12) United States Patent
Kishida et al.

(10) Patent No.: US 12,102,399 B2
(45) Date of Patent: Oct. 1, 2024

(54) SURGICAL ROBOT AND SURGICAL ROBOT SYSTEM

(71) Applicants: KAWASAKI JUKOGYO KABUSHIKI KAISHA, Kobe (JP); MEDICAROID CORPORATION, Kobe (JP)

(72) Inventors: Yuji Kishida, Kobe (JP); Tomohiro Fukuno, Kobe (JP); Ryosuke Hida, Kobe (JP); Tsuyoshi Tojo, Ibaraki (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 608 days.

(21) Appl. No.: 17/238,556

(22) Filed: Apr. 23, 2021

(65) Prior Publication Data
US 2021/0330403 A1 Oct. 28, 2021

(30) Foreign Application Priority Data
Apr. 28, 2020 (JP) .................................. 2020-079006

(51) Int. Cl.
*A61B 34/30* (2016.01)
*B25J 9/12* (2006.01)
*A61B 17/00* (2006.01)

(52) U.S. Cl.
CPC .............. *A61B 34/30* (2016.02); *B25J 9/12* (2013.01); *A61B 2017/00115* (2013.01)

(58) Field of Classification Search
CPC .......... A61B 34/30; A61B 2017/00115; A61B 2034/742; A61B 2090/0808; A61B 2090/0811; B25J 9/12
See application file for complete search history.

(56) References Cited

U.S. PATENT DOCUMENTS

| | | | |
|---|---|---|---|
| 8,479,969 B2 | 7/2013 | Shelton, IV | |
| 2007/0005045 A1* | 1/2007 | Mintz | B25J 19/00 606/1 |
| 2007/0048118 A1* | 3/2007 | Ogawa | B25J 5/007 414/467 |
| 2007/0142824 A1* | 6/2007 | Devengenzo | A61B 34/30 606/1 |
| 2018/0079090 A1* | 3/2018 | Koenig | G01L 3/14 |
| 2019/0160865 A1 | 5/2019 | Bhat et al. | |

FOREIGN PATENT DOCUMENTS

| | | |
|---|---|---|
| JP | 2008-544814 A | 12/2008 |
| JP | 2019-531216 A | 10/2019 |
| WO | 2007/005555 A2 | 1/2007 |
| WO | 2019/032582 A1 | 2/2019 |

* cited by examiner

*Primary Examiner* — Kira Nguyen
(74) *Attorney, Agent, or Firm* — METROLEX IP LAW GROUP, PLLC; Robert L. Scott, Esq.

(57) ABSTRACT

A surgical robot includes a first indicator configured to indicate a state of a system, and a plurality of second indicators configured to individually indicate states of a plurality of arms, and the state of the system includes a state of the surgical robot excluding the states of the plurality of arms and a state of a doctor-side operation device.

20 Claims, 6 Drawing Sheets

SURGICAL ROBOT AND SURGICAL ROBOT SYSTEM

CROSS-REFERENCE TO RELATED APPLICATION

The priority application number JP2020-079006, Surgical Robot and Surgical Robot System, Apr. 28, 2020, Yuji Kishida, Tomohiro Fukuno, Ryosuke Hida, and Tsuyoshi Tojo, upon which this patent application is based, is hereby incorporated by reference.

BACKGROUND OF THE INVENTION

Field of the Invention

The present disclosure relates to a surgical robot and a surgical robot system each including a plurality of arms.

Description of the Background Art

Conventionally, a surgical robot including a plurality of arms is known. Such a surgical robot is disclosed in Japanese Translation of PCT International Application Publication No. 2008-544814, for example.

Japanese Translation of PCT International Application Publication No. 2008-544814 discloses a robotic surgical system including a plurality of manipulators to which surgical tools are attached. In this robotic surgical system, each of the plurality of manipulators is supported by an alignment platform via a setup linkage arm. Furthermore, in this robotic surgical system, indicators are provided on the manipulators. The indicators include LEDs. Colors of light emitted by the LEDs and the light emission states represent the states of the manipulators, the states of the surgical tools, and the state of a system related to the manipulator. For example, yellow emission of the LEDs indicates a warning. Red emission of the LEDs indicates an obstacle to the operation of the manipulators. Red blinking of all the LEDs indicates that the battery power is exhausted. Blue emission of the LEDs indicates that the surgical tools are attached to the manipulators. The indicators (LEDs) are provided in the vicinity of interfaces for attaching the surgical tools of the plurality of manipulators.

However, in the robotic surgical system described in Japanese Translation of PCT International Application Publication No. 2008-544814, the indicators indicating a warning, for example, are provided on the plurality of manipulators, respectively. Therefore, an operator (such as an assistant doctor, a nurse, or a technician) who is working on the manipulator side during surgery needs to check indication (such as colors or light emission states) of the indicators provided on the plurality of manipulators, and it may be difficult to intuitively understand the contents of indication of the indicators. Thus, a surgical robot that allows an operator to intuitively understand whether indicators indicate the states of a plurality of manipulators (arms) or the state of a robotic surgical system is desired.

SUMMARY OF THE INVENTION

The present disclosure is intended to solve the above problem. The present disclosure aims to provide a surgical robot and a surgical robot system that each allow an operator to intuitively understand whether indicators indicate the state of a system or the states of a plurality of arms.

In order to attain the aforementioned object, a surgical robot according to a first aspect of the present disclosure includes a plurality of arms each configured to allow a medical device to be attached thereto, and an arm base configured to support the plurality of arms. The arm base includes a first indicator configured to indicate a state of a system including the surgical robot and a doctor-side operation device configured to remotely operate the plurality of arms, and a plurality of second indicators configured to individually indicate states of the plurality of arms, and the state of the system includes a state of the surgical robot excluding the states of the plurality of arms and a state of the doctor-side operation device.

In the surgical robot according to the first aspect of the present disclosure, as described above, the arm base configured to support the plurality of arms includes the first indicator that indicates the state of the system and the second indicators that individually indicate the states of the plurality of arms. Accordingly, the first indicator that indicates the state of the system and the plurality of second indicators that individually indicate the states of the plurality of arms can be arranged in a concentrated manner on the arm base (one member). Consequently, an operator can intuitively understand whether the state of the system or the states of the plurality of arms are indicated.

A surgical robot system according to a second aspect of the present disclosure includes a patient-side device, and a doctor-side operation device configured to remotely operate the patient-side device. The patient-side device includes a plurality of arms each configured to allow a medical device to be attached thereto, and an arm base configured to support the plurality of arms. The arm base includes a first indicator configured to indicate a state of the surgical robot system, and a plurality of second indicators configured to individually indicate states of the plurality of arms, and the state of the surgical robot system includes a state of the patient-side device excluding the states of the plurality of arms and a state of the doctor-side operation device.

In the surgical robot system according to the second aspect of the present disclosure, as described above, the arm base configured to support the plurality of arms includes the first indicator that indicates the state of the surgical robot system and the second indicators that individually indicate the states of the plurality of arms. Accordingly, the first indicator that indicates the state of the surgical robot system and the plurality of second indicators that individually indicate the states of the plurality of arms can be arranged in a concentrated manner on the arm base (one member). Consequently, an operator can intuitively understand whether the state of the surgical robot system or the states of the plurality of arms are indicated.

According to the present disclosure, as described above, the surgical robot that allows the operator to intuitively understand whether the indicators indicate the state of the system or the states of the plurality of arms is provided.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Figure 1:
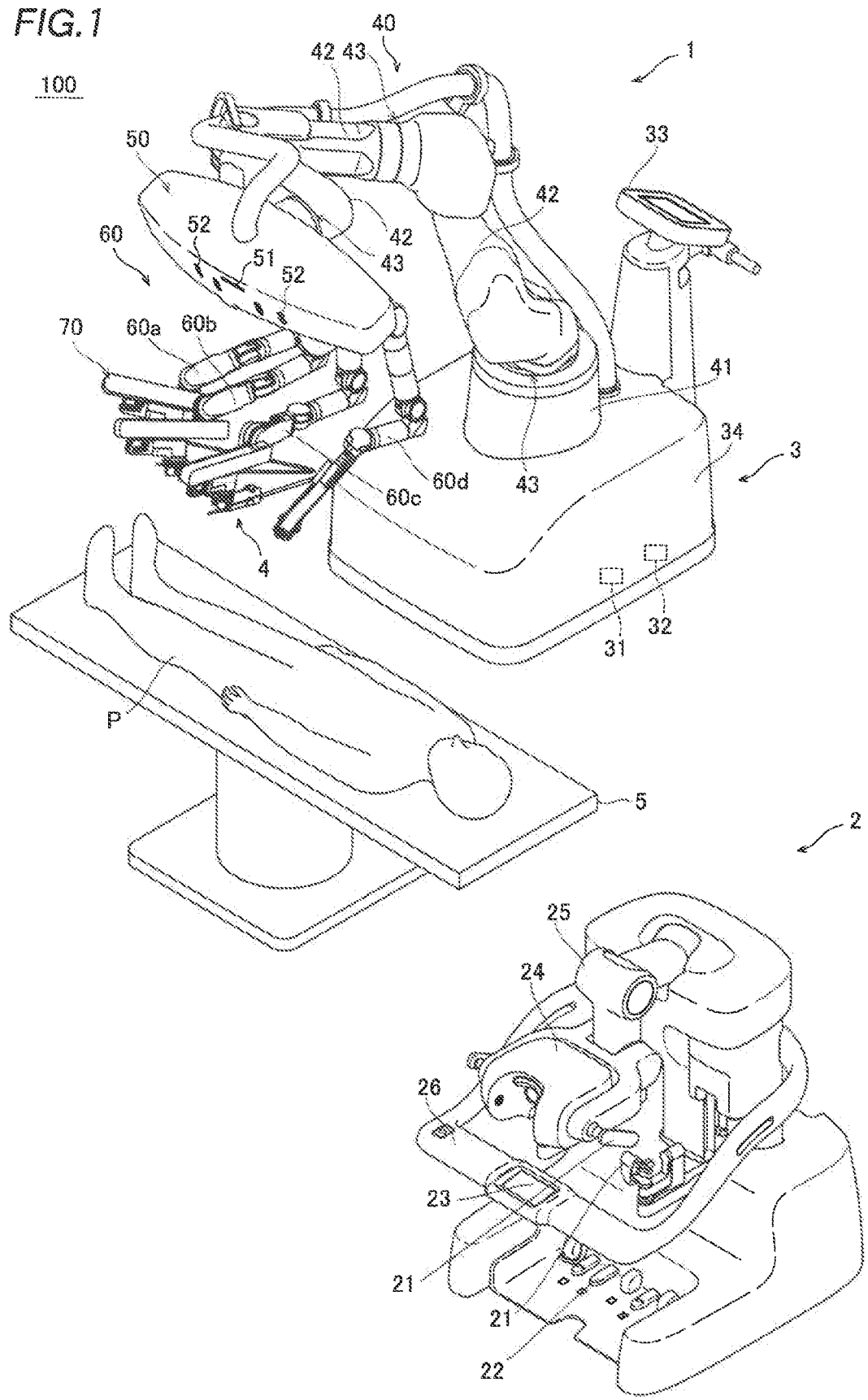
FIG. 1 is a diagram showing the configuration of a surgical system according to an embodiment of the present disclosure.

An embodiment of the present disclosure is hereinafter described with reference to the drawings.

The configuration of a surgical system 100 according to this embodiment is now described with reference to FIGS. 1 to 9. The surgical system 100 includes a medical manipulator 1 that is a patient P-side device and a remote operation device 2 that is an operator-side device configured to operate the medical manipulator 1. The medical manipulator 1 includes a medical cart 3 and is configured to be movable. The remote operation device 2 is spaced apart from the medical manipulator 1, and the medical manipulator 1 is configured to be remotely operated by the remote operation device 2. A surgeon inputs a command to the remote operation device 2 to cause the medical manipulator 1 to perform a desired operation. The remote operation device 2 transmits the input command to the medical manipulator 1. The medical manipulator 1 operates based on the received command. The medical manipulator 1 is arranged in an operating room that is a sterilized sterile field. The medical manipulator 1 is an example of a "surgical robot" or a "patient-side device" in the claims. The surgical system 100 is an example of a "system" in the claims. The remote operation device 2 is an example of a "doctor-side operation device" in the claims.

The remote operation device 2 is arranged inside or outside the operating room, for example. The remote operation device 2 includes operation manipulator arms 21, operation pedals 22, a touch panel 23, a monitor 24, a support arm 25, and a support bar 26. The remote operation device 2 is spaced apart from the medical manipulator 1 (a plurality of arms 60). The operation manipulator arms 21 define operation handles for the surgeon to input commands. The monitor 24 is a scope-type display that displays an image captured by an endoscope 6 (see FIG. 3). The support arm 25 supports the monitor 24 so as to align the height of the monitor 24 with the height of the surgeon's face. The touch panel 23 is arranged on the support bar 26. The surgeon's head is detected by a sensor (not shown) provided in the vicinity of the monitor 24 such that the medical manipulator 1 can be operated by the remote operation device 2. The surgeon operates the operation manipulator arms 21 and the operation pedals 22 while visually recognizing an affected area on the monitor 24. Thus, a command is input to the remote operation device 2. The command input to the remote operation device 2 is transmitted to the medical manipulator 1.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote operation device 2.

The medical cart 3 includes an input 33. The input 33 is configured to receive operations to move a positioner 40, an arm base 50, and the plurality of arms 60 or change their postures mainly in order to prepare for surgery before the surgery. The positioner 40 is an example of an "arm base mover" in the claims.

Figure 2:
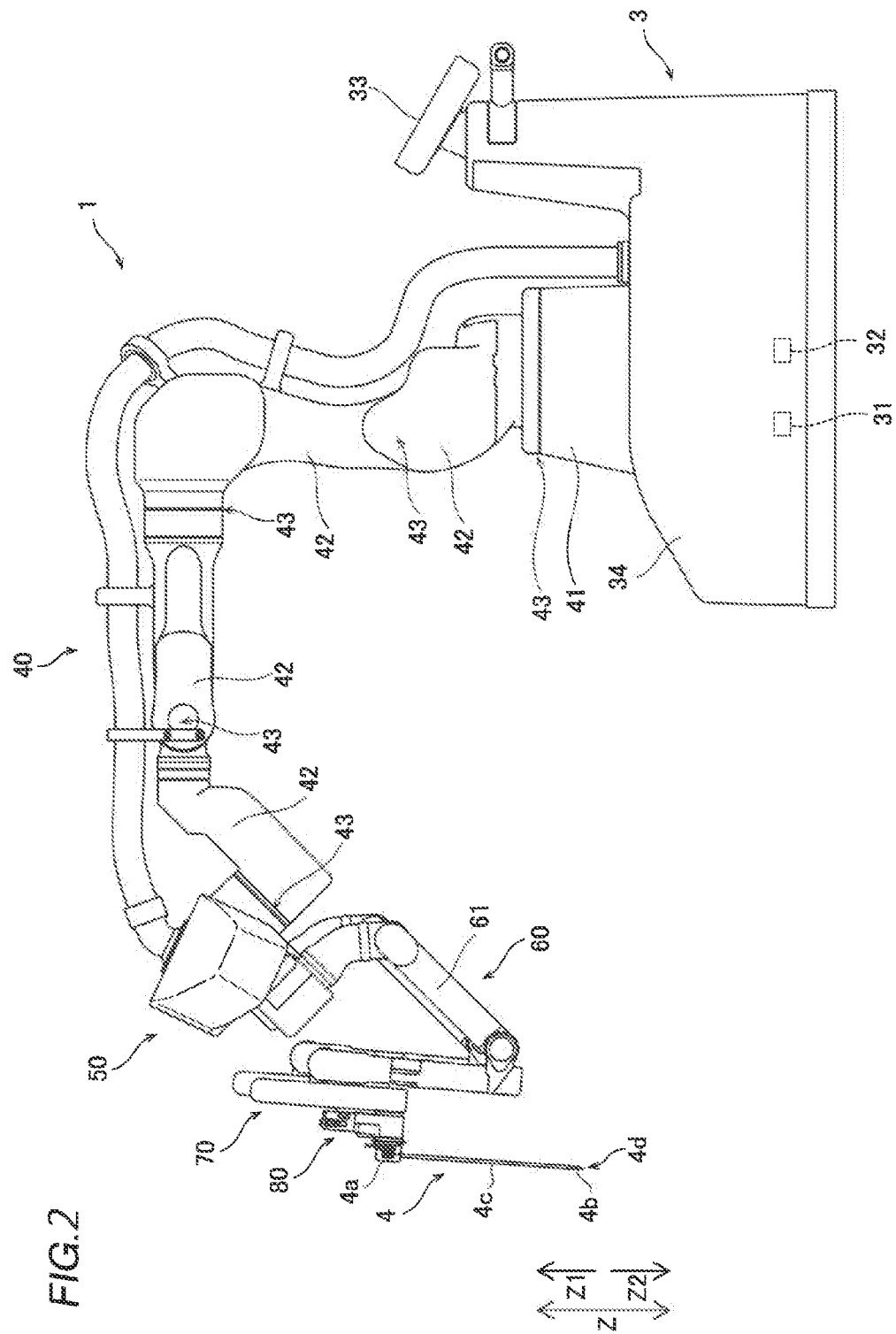
FIG. 2 is a diagram showing the configuration of a medical manipulator according to the embodiment of the present disclosure.

As shown in FIGS. 1 and 2, the medical manipulator 1 is arranged in the operating room. The medical manipulator 1 includes the medical cart 3, the positioner 40, the arm base 50, and the plurality of arms 60. The arm base 50 is attached to the tip end of the positioner 40. The arm base 50 has a relatively long rod shape (long shape). The bases of the plurality of arms 60 are attached to the arm base 50. Each of the plurality of arms 60 is configured to be able to take a folded posture (stored posture). The arm base 50 and the plurality of arms 60 are covered with sterile drapes (not shown) and used.

As shown in FIGS. 1 and 2, the positioner 40 includes a 7-axis articulated robot, for example. The positioner 40 is arranged on a casing 34 of the medical cart 3. The positioner 40 moves the arm base 50. Specifically, the positioner 40 is configured to move the position of the arm base 50 three-dimensionally.

The positioner 40 includes a base 41 and a plurality of links 42 coupled to the base 41. The plurality of links 42 are coupled to each other by joints 43.

Figure 3:
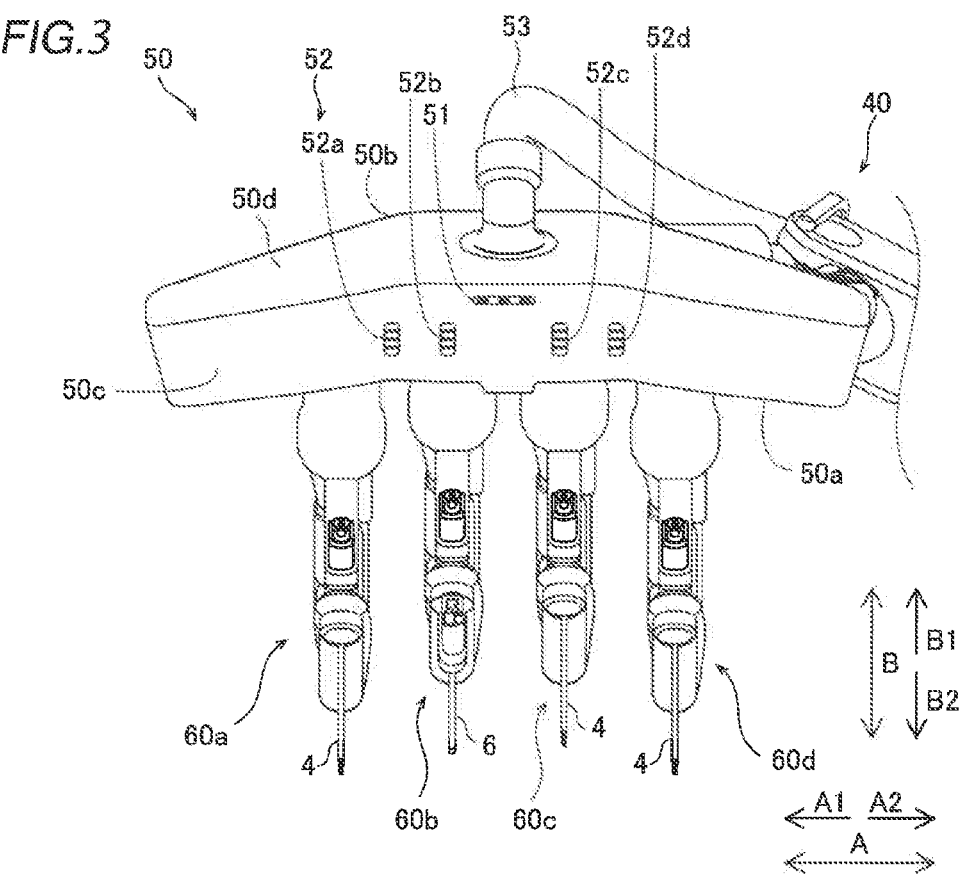
FIG. 3 is a diagram showing the configuration of indicators of the medical manipulator according to the embodiment of the present disclosure.

In this embodiment, as shown in FIG. 3, the arm base 50 includes a first indicator 51 that indicates the state of the surgical system 100 including the medical manipulator 1, which is a patient-side device, and the remote operation device 2, and second indicators 52 that individually indicate the states of the plurality of arms 60. The state of the surgical system 100 includes the state of the medical manipulator 1 excluding the states of the plurality of arms 60 and the state of the remote operation device 2. A plurality of second indicators 52 are provided so as to correspond to the plurality of arms 60. That is, four second indicators 52 are provided so as to correspond to four arms 60. The plurality of second indicators 52 are arranged along the arrangement of the plurality of arms 60 on the arm base 50. Specifically, the plurality of second indicators 52a to 52d are arranged in the order of the second indicators 52a to 52d from the A1 direction side toward the A2 direction side along the arrangement of the four arms 60a to 60d. An A direction refers to a direction along the long side of a substantially rectangular third surface 50c of the arm base 50.

In this embodiment, the arm base 50 has a first surface 50a by which the arms 60 are supported, a second surface 50b connected to the positioner 40, and the third surface 50c other than the first surface 50a and the second surface 50b. The first indicator 51 and the plurality of second indicators 52 are arranged on the third surface 50c. Specifically, the arm base 50 has a relatively long rod shape (substantially prismatic shape) as described above. The arms 60 are attached to the first surface 50a of the substantially prismatic arm base 50. The positioner 40 is connected to the second surface 50b that is substantially orthogonal to the first surface 50a. The first indicator 51 and the plurality of second indicators 52 are arranged on the third surface 50c that is substantially orthogonal to the first surface 50a and faces the second surface 50b. Furthermore, a harness 53 is connected to a fourth surface 50d that faces the first surface 50a.

In this embodiment, the first indicator 51 is arranged on a central portion of the third surface 50c. The plurality of second indicators 52 are arranged on both sides of the first indicator 51 on the third surface 50c. Specifically, the first indicator 51 is arranged on an upper (the B1 direction side) central portion of the third surface 50c. On the third surface 50c, the second indicators 52a and 52b are arranged on the A1 direction side of the first indicator 51. Furthermore, on the third surface 50c, the second indicators 52c and 52d are arranged on the A2 direction side of the first indicator 51. The plurality of second indicators 52a to 52d are arranged on a central portion in a B direction on the third surface 50c. The B direction refers to a direction orthogonal to the A direction. The plurality of arms 60 are attached to the B2 direction side of the arm base 50.

In this embodiment, each of the first indicator 51 and the second indicators 52 indicates the state of the surgical system 100 and the states of the arms 60 by at least one of an indicated color, blinking, or lighting. A specific description is given below.

Figure 4:
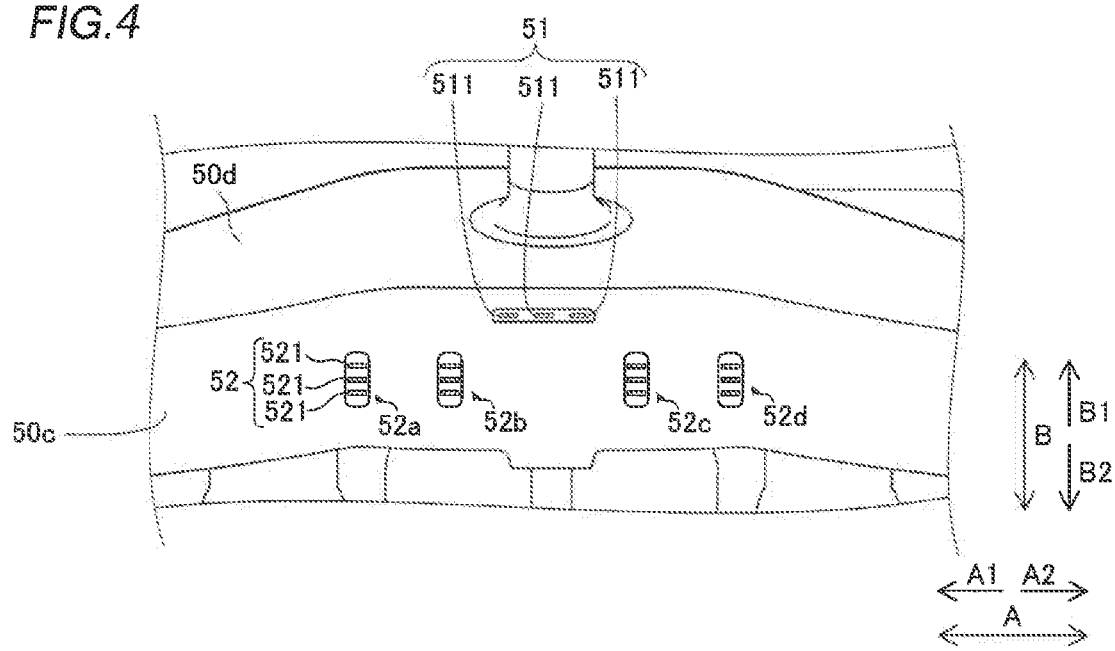
FIG. 4 is a partially enlarged view of FIG. 3.

In this embodiment, as shown in FIG. 4, the first indicator 51 includes a plurality of first indicator portions 511 that emit different colors of light. Each of the plurality of second indicators 52 includes a plurality of second indicator portions 521 that emit different colors of light. The first indicator portions 511 and the second indicator portions 521 include LEDs (light-emitting diodes). The first indicator portion 511 and the second indicator portions 521 may include light sources other than the LEDs. The plurality of first indicator portions 511 include three first indicator portions 511 that emit green, yellow, and red light, respectively. The second indicator portions 521 include three second indicator portions 521 that emit green, yellow, and red light, respectively.

In this embodiment, the plurality of first indicator portions 511 are arranged along the A direction. The plurality of second indicator portions 521 are arranged along the B direction orthogonal to the A direction. That is, on the third surface 50c, the three first indicator portions 511 are arranged in a line along the A direction. Furthermore, on the third surface 50c, the three second indicator portions 521 are arranged in a line along the B direction. The A direction and the B direction are examples of a "first direction" and a "second direction" in the claims, respectively.

In this embodiment, the first indicator 51 is configured to indicate at least one of information indicating that the surgical system 100 is normal, information indicating that the positioner 40 is in operation, error information on the surgical system 100, or caution information on the surgical system 100. Specifically, when the surgical system 100 is stopped, the first indicator 51 is turned off. The green lighting of the first indicator 51 indicates the information indicating that the surgical system 100 is normal. The green blinking of the first indicator 51 indicates the information indicating that the positioner 40 is in operation. The yellow lighting of the first indicator 51 indicates information indicating that a recoverable error is occurring in the surgical system 100. The yellow blinking of the first indicator 51 indicates information indicating that caution information for a user is being generated in the surgical system 100. The red lighting of the first indicator 51 indicates information indicating that an unrecoverable error is occurring in the surgical system 100. The red blinking of the first indicator 51 indicates that the surgical system 100 is undergoing emergency removal. That is, the first indicator 51 is configured to indicate information on the state of the surgical system 100, and the information on the state of the surgical system 100 includes information on the state of the medical manipulator 1, which is a patient-side device, excluding information on the states of the plurality of arms 60 and information on the state of the remote operation device 2, which is a doctor-side operation device.

In this embodiment, each of the second indicators 52 is configured to indicate at least one of information on whether or not a pivot position PP that serves as a fulcrum for movement of a medical device 4 attached to the arm 60 has been taught, error information on the arm 60, or caution information on the arm 60. Specifically, when the surgical system 100 is stopped, the second indicator 52 is turned off. The green lighting of the second indicator 52 indicates information indicating that the arm 60 is normal after teaching of the pivot position PP is completed. The pivot position PP refers to a position (see FIG. 8) that serves as a fulcrum for movement of the medical device 4 attached to the arm 60. The green blinking of the second indicator 52 (defined as a first blinking state) indicates information indicating that the arm 60 is normal when teaching of the pivot position PP is not completed. The green fast blinking of the second indicator 52 (defined as a second blinking state faster than the first blinking) indicates that an operation other than following is in progress. The following indicates that a predetermined number of times of use of the medical device 4 is added once. The yellow lighting of the second indicator 52 indicates information indicating that a recoverable error is occurring in the arm 60. The yellow lighting of the second indicator 52 indicates information indicating that caution information for the user is being generated in the arm 60. The red lighting of the second indicator 52 indicates information indicating that an unrecoverable error is occurring in the arm 60. Indication of the second indicator 52 described above is performed on the plurality of second indicators 52 so as to correspond to the states of the plurality of arms 60, respectively.

As shown in FIG. 1, the medical device 4 is attached to the tip end of each of the plurality of arms 60. The medical device 4 includes a replaceable instrument or the endoscope 6 (see FIG. 3), for example.

As shown in FIG. 2, the instrument as the medical device 4 includes a driven unit 4a driven by a servomotor M2 (see FIG. 9) provided in a holder 71 of each of the arms 60. An end effector 4b is provided at the tip end of the instrument. The end effector 4b includes a pair of forceps, a pair of scissors, a grasper, a needle holder, a microdissector, a stable applier, a tacker, a suction cleaning tool, a snare wire, a clip applier, etc. as instruments having joints. The end effector 4b includes a cutting blade, a cautery probe, a washer, a catheter, a suction orifice, etc. as instruments having no joint. The medical device 4 includes a shaft 4c that connects the driven unit 4a to the end effector 4b. The driven unit 4a, the shaft 4c, and the end effector 4b are arranged along a Z direction.

The configuration of the arms 60 is now described in detail.

Figure 5:
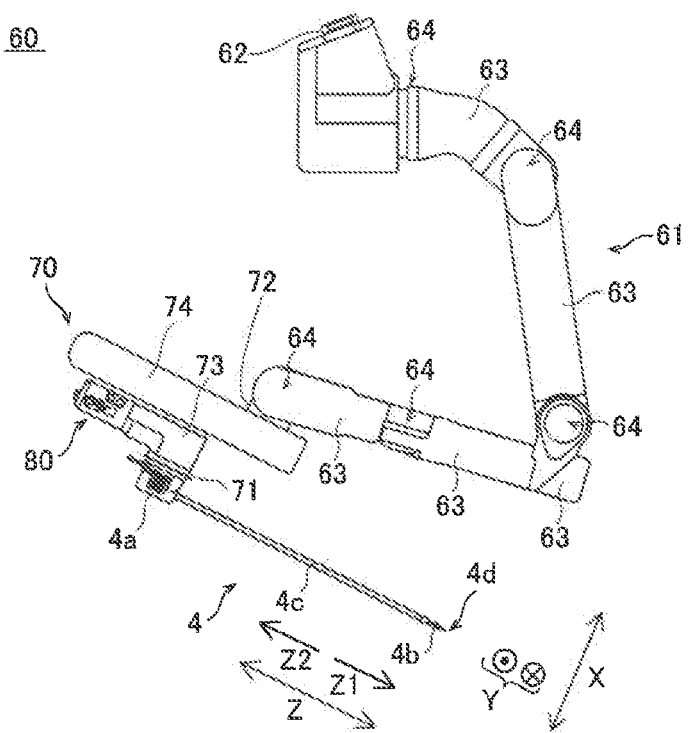
FIG. 5 is a diagram showing the configuration of an arm of the medical manipulator according to the embodiment of the present disclosure.

As shown in FIG. 5, each of the arms 60 includes an arm portion 61 (a base 62, links 63, and joints 64) and a translation mechanism 70 provided at the tip end of the arm portion 61. The arms 60 are configured to be able to three-dimensionally move the tip end sides with respect to the base sides (arm base 50) of the arms 60. The plurality of arms 60 have the same configuration as each other.

The translation mechanism 70 is provided on the tip end side of the arm portion 61, and the medical device 4 is attached thereto. The translation mechanism 70 translates the medical device 4 in a direction in which the medical device 4 is inserted into the patient P. Furthermore, the translation mechanism 70 is configured to translate the medical device 4 relative to the arm portion 61. Specifically, the translation mechanism 70 includes the holder 71 that holds the medical device 4. The servomotor M2 (see FIG. 9) is housed in the holder 71. The servomotor M2 is configured to rotate a rotating body provided in the driven unit 4a of the medical device 4. The rotating body of the driven unit 4a is rotated such that the end effector 4b is operated.

The arms 60 are configured to be removable from the arm base 50.

The arm portion 61 includes a 7-axis articulated robot arm. The arm portion 61 includes the base 62 configured to attach the arm portion 61 to the arm base 50, and a plurality of links 63 coupled to the base 62. The plurality of links 63 are coupled to each other by the joints 64.

The translation mechanism 70 is configured to translate the medical device 4 attached to the holder 71 along the Z direction (a direction in which the shaft 4c extends) by translating the holder 71 along the Z direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the Z direction. The tip end side link 73 is moved along the Z direction relative to the base end side link 72 such that the medical device 4 provided on the holder 71 is translated along the Z direction. The tip end of the arm portion 61 is connected to the base end side link 72 so as to rotate the base end side link 72 about a Y direction orthogonal to the Z direction.

As shown in FIG. 1, the endoscope 6 is attached to one (an arm 60b, for example) of the plurality of arms 60, and medical devices 4 other than the endoscope 6 are attached to the remaining arms 60 (arms 60a, 60c, and 60d, for example).

Figure 6:
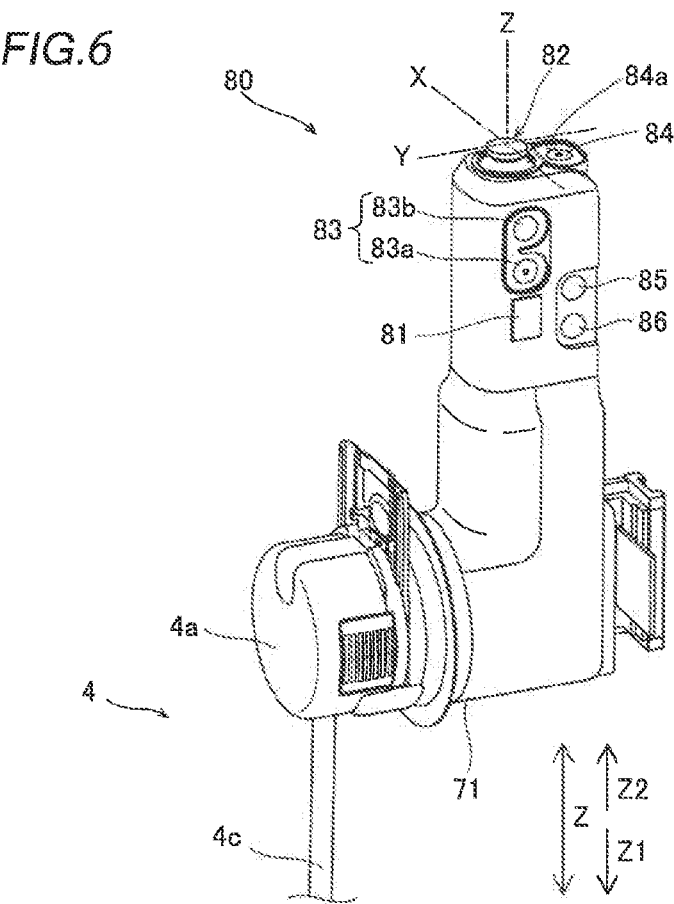
FIG. 6 is a perspective view showing the configuration of an operation unit of the medical manipulator according to the embodiment of the present disclosure.

As shown in FIG. 6, the medical manipulator 1 includes an operation unit 80 attached to each of the arms 60 to operate the arm 60. The operation unit 80 includes an enable switch 81, a joystick 82, and a switch unit 83. The enable switch 81 allows or disallows movement of the arm 60 through the joystick 82 and the switch unit 83. The enable switch 81 gets into a state of allowing movement of the medical device 4 by the arm 60 when an operator (such as a nurse or an assistant) grasps and presses the operation unit 80.

Specifically, the enable switch 81 is a push-button switch pressed by the operator's finger. The operator tilts the joystick 82 with their finger such that the joystick 82 is operated. The arm 60 is controlled to be moved according to a direction in which the joystick 82 is tilted and an angle at which the joystick 82 is tilted.

The joystick 82 is configured to operate movement of the medical device 4 by the arm 60 such that the tip end 4d (see FIG. 5) of the medical device 4 moves on a predetermined plane. The switch unit 83 is configured to operate movement of the medical device 4 by the arm 60 such that the tip end 4d of the medical device 4 moves along the longitudinal direction of the medical device 4 orthogonal to the predetermined plane. The switch unit 83 includes a switch 83a configured to move the tip end 4d of the medical device 4 in the direction in which the medical device 4 is inserted into the patient P along the longitudinal direction of the medical device 4, and a switch 83b configured to move the tip end 4d of the medical device 4 in a direction opposite to the direction in which the medical device 4 is inserted into the patient P.

The operation unit 80 includes a pivot button 85 configured to teach the pivot position PP that serves as a fulcrum for movement of the medical device 4 attached to the arm 60. Furthermore, an adjustment button 86 for optimizing the position of the arm 60 is provided on the operation unit 80.

The operation unit 80 includes a mode switching button 84 configured to switch between a mode for translating the medical device 4 attached to the arm 60 and a mode for rotating the medical device 4 attached to the arm 60. Furthermore, a mode indicator 84a is provided in the vicinity of the mode switching button 84. The mode indicator 84a indicates a switched mode.

Figure 7:
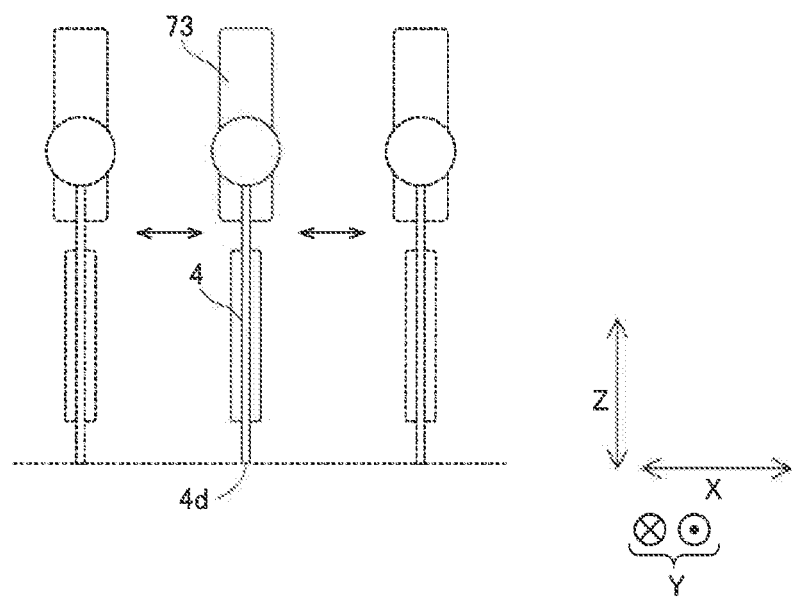
FIG. 7 is a diagram for illustrating translation of the arm.
Figure 8:
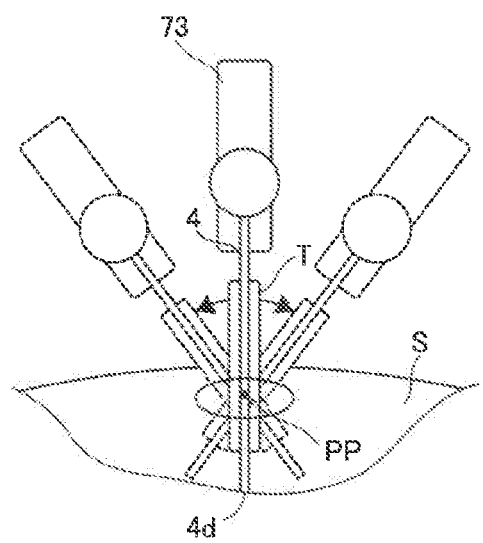
FIG. 8 is a diagram for illustrating rotation of the arm.

As shown in FIG. 7, in the mode for translating the arm 60, the arm 60 is moved such that the tip end 4d of the medical device 4 moves on an X-Y plane. As shown in FIG. 8, in the mode for rotating the arm 60, the arm 60 is moved such that the medical device 4 rotates about the pivot position PP as a fulcrum. The medical device 4 is rotated while the shaft 4c of the medical device 4 is inserted into a trocar T.

Figure 9:
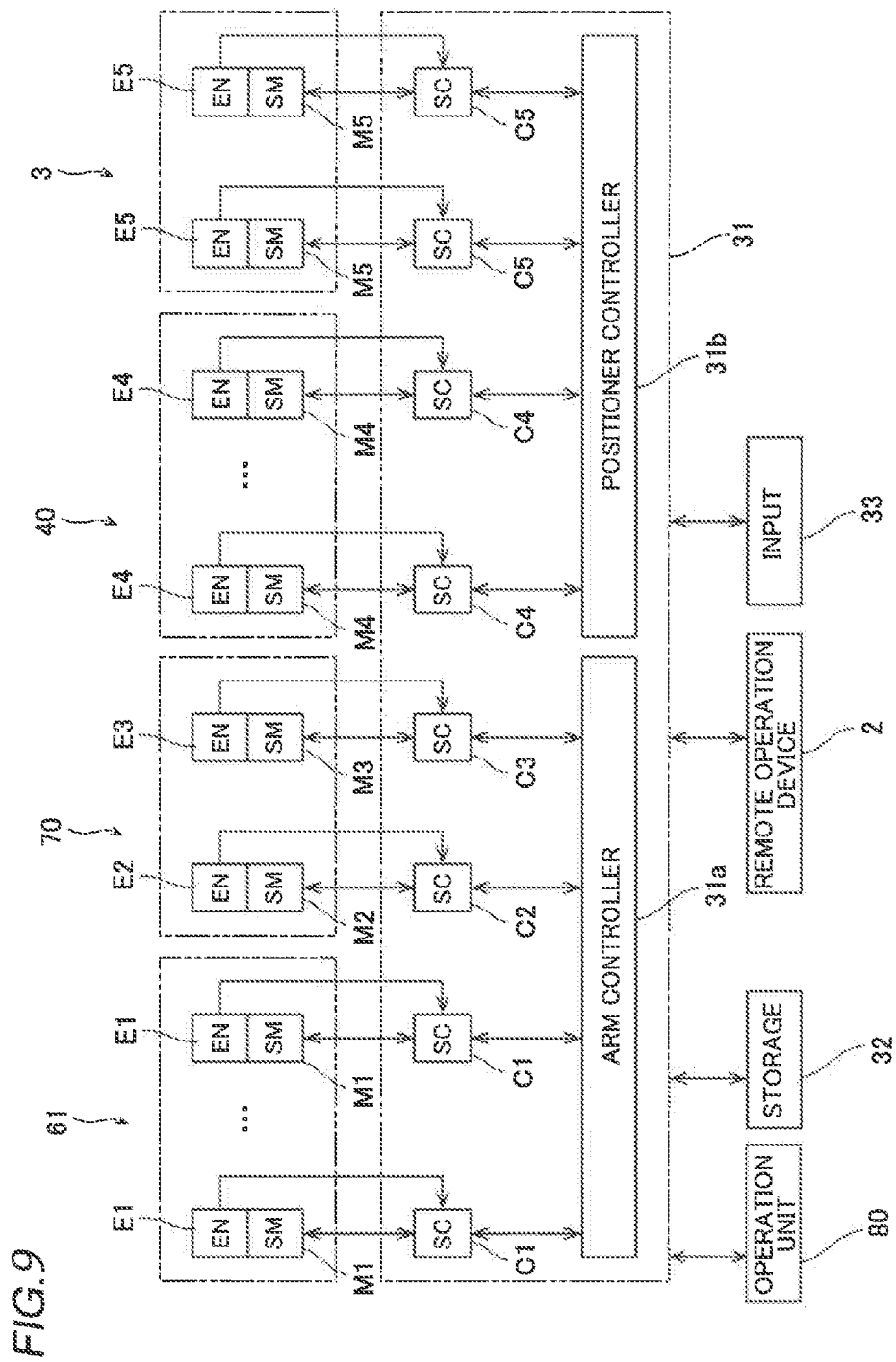
FIG. 9 is a block diagram showing the configuration of a controller of the medical manipulator according to the embodiment of the present disclosure.

As shown in FIG. 9, the arm 60 includes a plurality of servomotors M1, encoders E1, and speed reducers (not shown) so as to correspond to a plurality of joints 64 of the arm portion 61. The encoders E1 are configured to detect the rotation angles of the servomotors M1. The speed reducers are configured to slow down rotation of the servomotors M1 to increase the torques.

As shown in FIG. 9, the translation mechanism 70 includes the servomotor M2 configured to rotate the rotating body provided in the driven unit 4a of the medical device 4, a servomotor M3 configured to translate the medical device 4, encoders E2 and E3, and speed reducers (not shown). The encoders E2 and E3 are configured to detect the rotation angles of the servomotors M2 and M3, respectively. The speed reducers are configured to slow down rotation of the servomotors M2 and M3 to increase the torques.

The positioner 40 includes a plurality of servomotors M4, encoders E4, and speed reducers (not shown) so as to correspond to a plurality of joints 43 of the positioner 40. The encoders E4 are configured to detect the rotation angles of the servomotors M4. The speed reducers are configured to slow down rotation of the servomotors M4 to increase the torques.

The medical cart 3 includes servomotors M5 configured to drive a plurality of front wheels (not shown) of the medical cart 3, respectively, encoders E5, and speed reducers (not shown). The encoders E5 are configured to detect the rotation angles of the servomotors M5. The speed reducers are configured to slow down rotation of the servomotors M5 to increase the torques.

The controller 31 of the medical cart 3 includes an arm controller 31a that controls movement of the plurality of arms 60 based on commands, and a positioner controller 31b that controls movement of the positioner 40 and driving of the front wheels (not shown) of the medical cart 3 based on commands.

The arm controller 31a outputs an operation command to a corresponding servo controller of a plurality of servo controllers described below based on an operation input to the remote operation device 2, and the corresponding servo controller operates a plurality of servomotors of the corresponding arm 60 based on the operation command.

The arm controller 31a outputs an operation command to a servo controller described below corresponding to one of the plurality of arms 60 based on an operation input to the operation unit 80 of the arm 60, and the corresponding servo controller operates a plurality of servomotors of the arm 60 based on the operation command.

Specifically, servo controllers C1 configured to control the servomotors M1 configured to drive the arm 60 are electrically connected to the arm controller 31a. The encoders E1 configured to detect the rotation angles of the servomotors M1 are electrically connected to the servo controllers C1.

A servo controller C2 configured to control the servomotor M2 configured to drive the medical device 4 is electrically connected to the arm controller 31a. The encoder E2 configured to detect the rotation angle of the servomotor M2 is electrically connected to the servo controller C2. A servo controller C3 configured to control the servomotor M3 configured to translate the translation mechanism 70 is electrically connected to the arm controller 31a. The encoder E3 configured to detect the rotation angle of the servomotor M3 is electrically connected to the servo controller C3.

An operation command input to the remote operation device 2 is input to the arm controller 31a. The arm controller 31a generates position commands based on the input operation command and the rotation angles detected by the encoders E1 (E2 or E3), and outputs the position commands to the servo controllers C1 (C2 or C3). The servo controllers C1 (C2 or C3) generate torque commands based on the position commands input from the arm controller 31a and the rotation angles detected by the encoders E1 (E2 or E3), and output the torque commands to the servomotors M1 (M2 or M3). Thus, the arm 60 is moved according to the operation command input to the remote operation device 2.

The controller 31 (arm controller 31a) is configured to operate the arm 60 based on an input signal from the joystick 82 of the operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate torque commands based on the position commands input from the arm controller 31a and the rotation angles detected by the encoders E1, and output the torque commands to the servomotors M1. Thus, the arm 60 is moved according to the operation command input to the joystick 82.

The controller 31 (arm controller 31a) is configured to operate the arm 60 based on an input signal from the switch unit 83 of the operation unit 80. Specifically, the arm controller 31a generates a position command(s) based on the input signal (operation command) input from the switch unit 83 and the rotation angle(s) detected by the encoders E1 or the encoder E3, and outputs the position command(s) to the servo controllers C1 or the servo controller C3. The servo controllers C1 or the servo controller C3 generates a torque command(s) based on the position command(s) input from the arm controller 31a and the rotation angle(s) detected by the encoders E1 or the encoder E3, and outputs the torque command(s) to the servomotors M1 or the servomotor M3.

Thus, the arm 60 is moved according to the operation command input to the switch unit 83.

As shown in FIG. 9, servo controllers C4 configured to control the servomotors M4 that move the positioner 40 are electrically connected to the positioner controller 31b. The encoders E4 configured to detect the rotation angles of the servomotors M4 are electrically connected to the servo controllers C4. Servo controllers C5 configured to control the servomotors M5 that drive the front wheels (not shown) of the medical cart 3 are electrically connected to the positioner controller 31b. The encoders E5 configured to detect the rotation angles of the servomotors M5 are electrically connected to the servo controllers C5.

An operation command regarding preparation position setting, for example, is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate torque commands based on the position commands input from the positioner controller 31b and the rotation angles detected by the encoders E4, and output the torque commands to the servomotors M4. Thus, the positioner 40 is moved according to the operation command input to the input 33. Similarly, the positioner controller 31b moves the medical cart 3 based on an operation command from the input 33.

Advantages of this Embodiment

According to this embodiment, the following advantages are achieved.

According to this embodiment, as described above, the arm base 50 configured to support the plurality of arms 60 includes the first indicator 51 that indicates the state of the surgical system 100 and the second indicators 52 that individually indicate the states of the plurality of arms 60. Accordingly, the first indicator 51 that indicates the state of the surgical system 100 and the plurality of second indicators 52 that individually indicate the states of the plurality of arms 60 can be arranged in a concentrated manner on the arm base 50 (one member). Consequently, the operator can intuitively understand whether the indicators (the first indicator 51 and the second indicators 52) indicate the state of the surgical system 100 or the states of the plurality of arms 60.

According to this embodiment, as described above, the plurality of the second indicators 52 are provided so as to correspond to the plurality of arms 60, and the plurality of second indicators 52 are arranged along the arrangement of the plurality of arms 60 on the arm base 50. Accordingly, the plurality of second indicators 52 are arranged along the arrangement of the plurality of arms 60, and thus the operator can easily confirm which second indicator 52 indicates the state of which arm 60.

According to this embodiment, as described above, the medical manipulator 1 includes the positioner 40 that moves the arm base 50, the arm base 50 includes the first surface 50a by which the arms 60 are supported, the second surface 50b connected to the positioner 40, and the third surface 50c other than the first surface 50a and the second surface 50b, and the first indicator 51 and the plurality of second indicators 52 are arranged on the third surface 50c. Accordingly, the first indicator 51 and the plurality of second indicators 52 are arranged on the surface different from the surfaces to which the arms 60 and the positioner 40 are connected among the surfaces of the arm base 50, and thus blocking of the indications (light emission) of the first indicator 51 and the plurality of second indicators 52 by the arms 60 and the positioner 40 can be significantly reduced or prevented.

According to this embodiment, as described above, the first indicator 51 is arranged on the central portion of the third surface 50c, and the plurality of second indicators 52 are arranged on both sides of the first indicator 51 on the third surface 50c. Accordingly, the second indicators 52 are arranged on both sides with the first indicator 51 as the center, and thus the first indicator 51 and the plurality of second indicators 52 can be easily checked at the same time unlike a case in which the plurality of second indicators 52 are biased with respect to the first indicator 51.

According to this embodiment, as described above, the first indicator 51 and the second indicators 52 are configured to indicate the state of the surgical system 100 and the states of the arms 60, respectively, by at least one of indicated colors, blinking, or lighting. Accordingly, the states can be easily checked by at least one of the colors, blinking, or lighting of the first indicator 51 and the second indicators 52.

According to this embodiment, as described above, the first indicator 51 includes the plurality of first indicator portions 511 that emit different colors of light, each of the plurality of second indicators 52 includes the plurality of second indicator portions 521 that emit different colors of light, the plurality of first indicator portions 511 are arranged along the A direction, and the plurality of second indicator portions 521 are arranged along the B direction orthogonal to the A direction. Accordingly, the arrangement direction of the indicator portions is different between the first indicator 51 and the second indicators 52, and thus the states can be checked while the first indicator 51 and the second indicators 52 are easily distinguished.

According to this embodiment, as described above, the medical manipulator 1 includes the positioner 40 including a robot that moves the arm base 50, and the first indicator 51 is configured to indicate at least one of the information indicating that the surgical system 100 is normal, the information indicating that the positioner 40 is in operation, the error information on the surgical system 100, or the caution information on the surgical system 100. Accordingly, the state of the entire surgical system 100 can be easily indicated by the first indicator 51.

According to this embodiment, as described above, each of the second indicators 52 is configured to indicate at least one of the information on whether or not the pivot position PP that serves as a fulcrum for movement of the medical device 4 attached to the arm 60 has been taught, the error information on the arm 60, or the caution information on the arm 60. Accordingly, the state of each of the arms 60 can be individually indicated by each of the plurality of second indicators 52.

Modified Examples

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the plurality of second indicators 52 are arranged along the arrangement of the plurality of arms 60 (along the A direction) on the arm base 50 in the aforementioned embodiment, the present disclosure is not limited to this. For example, the plurality of second indicators 52 may alternatively be arranged along the B direction.

While the first indicator 51 and the plurality of second indicators 52 are arranged on the third surface 50c of the arm base 50 in the aforementioned embodiment, the present disclosure is not limited to this. For example, the first indicator 51 and the plurality of second indicators 52 may alternatively be arranged on a surface other than the third surface 50c of the arm base 50. Furthermore, the first indicator 51 and the plurality of second indicators 52 may alternatively be arranged on different surfaces of the arm base 50.

While the first indicator 51 is arranged on the central portion of the third surface 50c, and the plurality of second indicators 52 are arranged on both sides of the first indicator 51 in the aforementioned embodiment, the present disclosure is not limited to this. For example, the first indicator 51 and the plurality of second indicators 52 may alternatively be arranged in the order of the first indicator 51 and the plurality of second indicators 52 along the A direction.

While the plurality of first indicator portions 511 are arranged along the A direction, and the plurality of second indicator portions 521 are arranged along the B direction in the aforementioned embodiment, the present disclosure is not limited to this. For example, the plurality of first indicator portions 511 may alternatively be arranged along the B direction, and the plurality of second indicator portions 521 may alternatively be arranged along the A direction.

While the first indicator 51 indicates all of the information indicating that the surgical system 100 is normal, the information indicating that the positioner 40 is in operation, the error information on the surgical system 100, and the caution information on the surgical system 100 in the aforementioned embodiment, the present disclosure is not limited to this. For example, the first indicator 51 may alternatively be configured to indicate one (or more but not all) of the information indicating that the surgical system 100 is normal, the information indicating that the positioner 40 is in operation, the error information on the surgical system 100, and the caution information on the surgical system 100. Furthermore, the first indicator 51 may alternatively indicate information other than the information described above.

While each of the second indicators 52 indicates all of the information on whether or not the pivot position PP has been taught, the error information on the arm 60, and the caution information on the arm 60 in the aforementioned embodiment, the present disclosure is not limited to this. For example, each of the second indicators 52 may alternatively be configured to indicate one (or more but not all) of the information on whether or not the pivot position PP has been taught, the error information on the arm 60, and the caution information on the arm 60. Furthermore, each of the second indicators 52 may alternatively indicate information other than the information described above.

While the four arms 60 are provided in the aforementioned embodiment, the present disclosure is not limited to this. The number of arms 60 may alternatively be three.

While each of the arm portion 61 and the positioner 40 includes a 7-axis articulated robot in the aforementioned embodiment, the present disclosure is not limited to this. For example, each of the arm portion 61 and the positioner 40 may alternatively include an articulated robot having an axis configuration (six axes or eight axes, for example) other than the 7-axis articulated robot.

What is claimed is:

1. A surgical robot comprising:
a plurality of arms each configured to allow a medical device to be attached thereto; and
an arm base configured to support the plurality of arms, wherein:
the arm base includes a first indicator configured to indicate a state of a system including the surgical robot and a doctor-side operation device configured to remotely operate the plurality of arms, and a plurality of second indicators in a fixed arrangement on the arm base despite movement of the plurality of the arms and configured to individually indicate states of the plurality of arms;
the first indicator and the plurality of second indicators are in the fixed arrangement on the arm base and concentrated in a same area on the arm base; and
the state of the system includes a state of the surgical robot excluding the states of the plurality of arms and a state of the doctor-side operation device.

2. The surgical robot according to claim 1, wherein
the plurality of second indicators are provided so as to correspond to the plurality of arms; and
the plurality of second indicators are arranged along an arrangement of the plurality of arms on the arm base.

3. The surgical robot according to claim 1, further comprising:
an arm base mover configured to move the arm base; wherein
the arm base includes a first surface by which the plurality of arms are supported, a second surface connected to the arm base mover, and a third surface other than the first surface and the second surface; and
the first indicator and the plurality of second indicators are arranged on the third surface.

4. The surgical robot according to claim 3, wherein
the first indicator is arranged on a central portion of the third surface; and
the plurality of second indicators are arranged on both sides of the first indicator on the third surface.

5. The surgical robot according to claim 1, wherein the first indicator and the second indicators are configured to indicate the state of the system and the states of the plurality of arms, respectively, by at least one of indicated colors, blinking, or lighting.

6. The surgical robot according to claim 1, wherein
the plurality of second indicators are provided so as to correspond to the plurality of arms;
the first indicator includes a plurality of first indicator portions configured to emit different colors of light;
each of the plurality of second indicators includes a plurality of second indicator portions configured to emit different colors of light;
the plurality of first indicator portions are arranged along a first direction; and
the plurality of second indicator portions are arranged along a second direction orthogonal to the first direction.

7. The surgical robot according to claim 1, further comprising:
an arm base mover including a robot configured to move the arm base; wherein
the first indicator is configured to indicate at least one of information indicating that the system is normal, information indicating that the arm base mover is in operation, error information on the system, or caution information on the system.

8. The surgical robot according to claim 1, wherein each of the second indicators is configured to indicate at least one of information on whether or not a pivot position that serves as a fulcrum for movement of the medical device attached to each of the plurality of arms has been taught, error information on the plurality of arms, or caution information on the plurality of arms.

9. A surgical robot system comprising:
a patient-side device; and
a doctor-side operation device configured to remotely operate the patient-side device; wherein;
the patient-side device includes:
a plurality of arms each configured to allow a medical device to be attached thereto; and
an arm base configured to support the plurality of arms;
the arm base includes a first indicator configured to indicate a state of the surgical robot system, and a plurality of second indicators in a fixed arrangement on the arm base despite movement of the plurality of the arms and configured to individually indicate states of the plurality of arms;
the first indicator and the plurality of second indicators are in the fixed arrangement on the arm base and concentrated in a same area on the arm base; and
the state of the surgical robot system includes a state of the patient-side device excluding the states of the plurality of arms and a state of the doctor-side operation device.

10. The surgical robot system according to claim 9, wherein
the plurality of second indicators are provided so as to correspond to the plurality of arms; and
the plurality of second indicators are arranged along an arrangement of the plurality of arms on the arm base.

11. The surgical robot system according to claim 9, further comprising:
an arm base mover configured to move the arm base; wherein
the arm base includes a first surface by which the plurality of arms are supported, a second surface connected to the arm base mover, and a third surface other than the first surface and the second surface; and
the first indicator and the plurality of second indicators are arranged on the third surface.

12. The surgical robot system according to claim 11, wherein
the first indicator is arranged on a central portion of the third surface; and
the plurality of second indicators are arranged on both sides of the first indicator on the third surface.

13. A surgical robot system comprising:
a patient-side device;
a doctor-side operation device configured to remotely operate the patient-side device; and
a controller configured to control operation of the patient-side device based on an operation input to the doctor-side operation device; wherein:
the patient-side device includes:
a plurality of arms each configured to allow a medical device to be attached thereto; and
an arm base configured to support the plurality of arms;
the arm base includes a first indicator configured to indicate a state of the surgical robot system, and a plurality of second indicators in a fixed arrangement on the arm base despite movement of the plurality of the arms and configured to individually indicate states of the plurality of arms;

the first indicator and the plurality of second indicators are in the fixed arrangement on the arm base and concentrated in a same area on the arm base; and the state of the surgical robot system includes a state of the patient-side device excluding the states of the plurality of arms and a state of the doctor-side operation device.

14. The surgical robot system according to claim 13, wherein each of the plurality of arms includes a plurality of joints and a plurality of servomotors corresponding to the plurality of joints.

15. The surgical robot system according to claim 14, further comprising:
   a plurality of servo controllers corresponding to the plurality of arms, respectively; wherein
   the controller is configured to output an operation command to a corresponding servo controller among the plurality of servo controllers based on the operation input to the doctor-side operation device; and
   the corresponding servo controller is configured to operate the plurality of servomotors of a corresponding arm based on the operation command.

16. The surgical robot system according to claim 13, wherein
   each of the plurality of arms includes an operation unit; and
   the controller is configured to move a corresponding arm based on an operation input to the operation unit.

17. The surgical robot system according to claim 16, wherein
   each of the plurality of arms includes a plurality of joints and a plurality of servomotors corresponding to the plurality of joints;

the surgical robot system further comprises a plurality of servo controllers corresponding to the plurality of arms, respectively;
   the controller is configured to output an operation command to a servo controller corresponding to one of the plurality of arms based on the operation input to the operation unit of the arm; and
   the corresponding servo controller is configured to operate the plurality of servomotors of the arm based on the operation command.

18. The surgical robot system according to claim 13, wherein
   the plurality of second indicators are provided so as to correspond to the plurality of arms; and
   the plurality of second indicators are arranged along an arrangement of the plurality of arms on the arm base.

19. The surgical robot system according to claim 18, further comprising:
   an arm base mover configured to move the arm base; wherein
   the arm base includes a first surface by which the plurality of arms are supported, a second surface connected to the arm base mover, and a third surface other than the first surface and the second surface; and
   the first indicator and the plurality of second indicators are arranged on the third surface.

20. The surgical robot system according to claim 19, wherein
   the first indicator is arranged on a central portion of the third surface; and
   the plurality of second indicators are arranged on both sides of the first indicator on the third surface.

* * * * *